United States Patent [19]

Sidebotham et al.

[11] Patent Number: 5,007,933
[45] Date of Patent: Apr. 16, 1991

[54] MODULAR KNEE PROSTHESIS SYSTEM

[75] Inventors: Christopher G. Sidebotham, Middletown, N.Y.; Donald E. McNulty, Warsaw, Ind.; Alan M. Lombardo, Elmwood Park, N.J.

[73] Assignee: Osteonics Corp., Allendale, N.J.

[21] Appl. No.: 304,754

[22] Filed: Jan. 31, 1989

[51] Int. Cl.⁵ ............................ A61F 2/38; A61F 2/30
[52] U.S. Cl. ............................................ 623/20; 623/18
[58] Field of Search ............................... 623/16, 18, 20

[56] References Cited

U.S. PATENT DOCUMENTS

| | | | |
|---|---|---|---|
| 4,001,896 | 1/1977 | Arkangel | 623/20 X |
| 4,213,209 | 7/1980 | Insall et al. | 623/20 |
| 4,224,697 | 9/1980 | Murray et al. | 623/20 |
| 4,257,129 | 3/1981 | Volz | 623/20 |
| 4,298,992 | 11/1981 | Burstein et al. | 623/20 |
| 4,309,778 | 1/1982 | Buechel et al. | 623/20 |
| 4,340,978 | 7/1982 | Buechel et al. | 623/20 |
| 4,470,158 | 9/1984 | Pappas et al. | 623/18 X |
| 4,501,031 | 2/1985 | McDaniel et al. | 623/20 |
| 4,634,444 | 1/1987 | Noiles | 623/20 |
| 4,795,468 | 1/1989 | Hodorek et al. | 623/20 X |

Primary Examiner—Richard J. Apley
Assistant Examiner—Linda C. M. Dvorak
Attorney, Agent, or Firm—Samuelson & Jacob

[57] ABSTRACT

A knee prosthesis system includes a tibial component having a tray element, a femoral component having laterally spaced apart condylar elements, a modular bearing member for being selected and seated within the tray element of the tibial component to provide a bearing support for the condylar elements of the femoral component for operation of the knee prothesis, the bearing member including an eminence projecting superiorly for reception between the condylar elements of the femoral component to provide controlled restraint against excessive relative movement between the femoral component and the tibial component, including control of the anterior-posterior portions of the relative movement, and a stabilizing post within the eminence for reinforcing and stabilizing the eminence against forces exerted upon the eminence during operation of the knee prosthesis.

22 Claims, 4 Drawing Sheets

MODULAR KNEE PROSTHESIS SYSTEM

The present invention relates generally to prosthetic implant devices used for replacing natural joints in the body and pertains, more specifically, to a knee prosthesis system for use in replacement of the natural knee joint with a prosthetic knee.

In the development of prosthetic implants for replacement of the natural knee joint, the stabilized knee prosthesis has exhibited desirable characteristics by way of enabling simulation of the movements allowed by the natural knee, while providing the advantage of added control of motion for resisting unwanted displacements and even dislocation, particularly where the tendons and ligaments available at the implant site no longer are adequate to provide the required stability. Generally, stability is attained by the introduction of structural features which tend to reduce the freedom of motion required to simulate natural movements, and stabilized knee prostheses have constituted a compromise between restoring the knee to its full normal function and providing a prosthetic knee joint which has adequate strength to withstand the loads imparted during service and the stability to resist dislocation of the components of the prosthesis under the conditions encountered during use.

The present invention is directed to a knee prosthesis of the type which his stabilized by structural features of the prosthetic implant components, and provides a knee prosthesis system having several objects and advantages, some of which may be summarized as follows: Freedom of motion to simulate movements available in the natural knee joint so as to restore more fully the natural function of the knee, while providing the stability necessary to resist unwanted movements and dislocation; requisite strength to withstand the stresses encountered during service, without excessive wear or catastrophic failure; facilitates the implant procedure, as well as any subsequent revision of the knee prosthesis which may become necessary, by providing a modular construction which enables adjustments in fit and in the degree of constraint through the selection and interoperative insertion of an appropriate tibial bearing member, independent of the implant of the femoral component and the tibial component of the prosthetic implant; requires minimal bone resection and attains a concomitant reduction in the invasion of the natural bone; is less sensitive to precise placement, thereby simplifying the implant procedure; accommodates some misalignment of the components of the prosthesis, without compromising performance; and provides exceptional performance over an extended service life.

The above objects and advantages, as well as further objects and advantages, are attained by the present invention which may be described briefly as an improvement in a knee prosthesis system for a prosthetic knee, the knee prosthesis system including a tibial component having a tray element, a femoral component having laterally spaced apart condylar elements, and a selectable bearing member to be carried by the tray element of the tibial component for supporting the condylar elements of the femoral component for operation of the knee prosthesis, including flexion of the prosthetic knee, the bearing member having an integral eminence projecting superiorly longitudinally upwardly from an inferior end adjacent the tibial component toward a superior end adjacent the femoral component for reception between the condylar elements of the femoral component to provide controlled restraint against excessive relative movement between the femoral component and the tibial component, control of the anterior-posterior portions of the relative movement being provided by a cam surface on the eminence and a follower on the femoral component for following the cam surface, the improvement comprising: a stabilizing post including a stabilizing portion for projecting superiorly from the tibial component toward the femoral component; and a recess in the eminence, the recess including a recess portion complementary to the stabilizing portion of the stabilizing post so that when the bearing member is seated on the tray element of the tibial component, the stabilizing portion of the stabilizing post is located within the recess portion of the recess to reinforce and stabilize the eminence against forces exerted upon the eminence during operation of the knee prosthesis.

The invention will be understood more fully, while still further objects and advantages will become apparent, in the following detailed description of a preferred embodiment of the invention illustrated in the accompanying drawing, in which.

Figure 6:
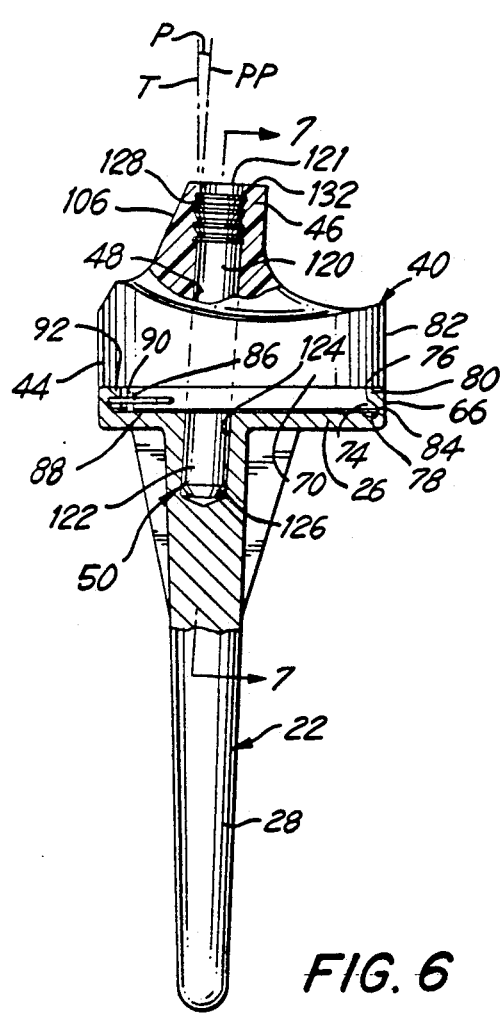
FIG. 6 is a side elevational view, partially sectioned, showing the tibial bearing member affixed to the tibial component of the knee prosthesis.
Figure 7:
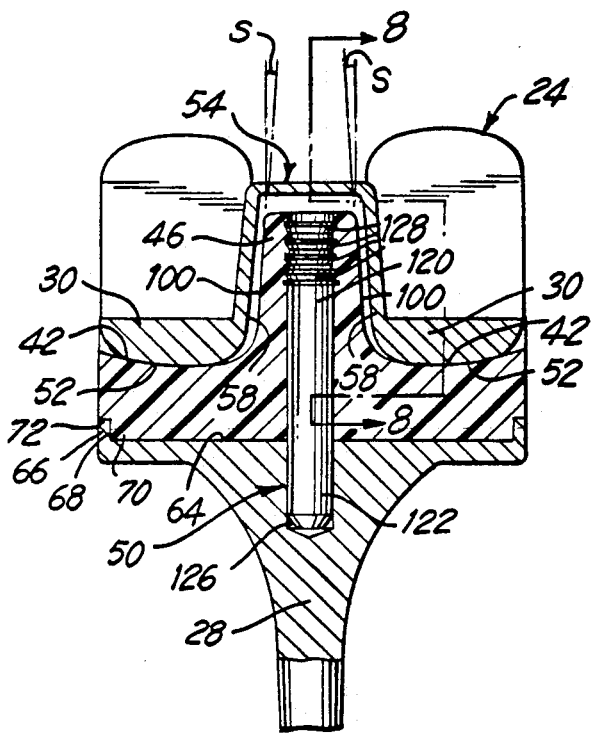

FIG. 7 is a fragmentary, longitudinal cross-sectional view taken along line 7—7 of FIG. 6, with the addition of the femoral component; and FIGS. 8 through 17 are somewhat diagrammatic, fragmentary cross-sectional views taken along line 8—8 of FIG. 7, illustrating flexion of the knee prosthesis.

Figure 1:
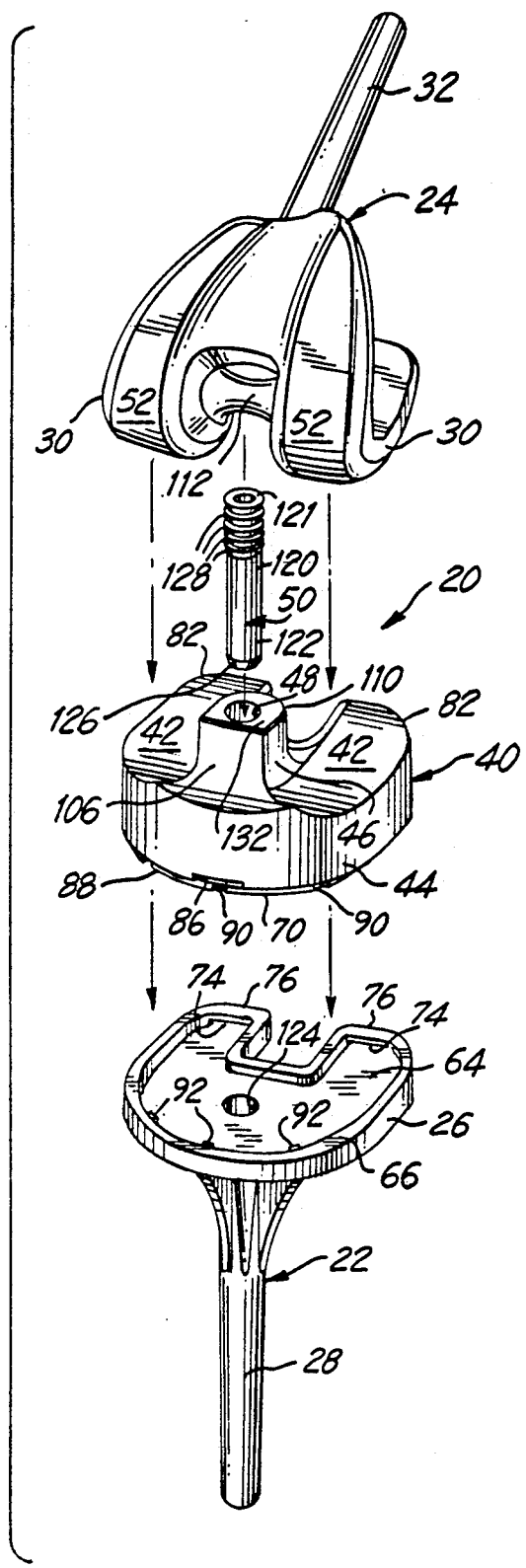
FIG. 1 is an exploded perspective view of a knee prosthesis constructed in accordance with the present invention.

Referring now to the drawing, and especially to FIG. 1 thereof, a knee prosthesis constructed in accordance with the invention is illustrated at 20 and is seen to include a tibial component 22 and a femoral component 24. Tibial component 22 has a tray element 26 and a stem 28 unitary with and depending inferiorly longitudinally downwardly from the tray element 26 for affixation in the natural tibia (not shown) in a manner now wellknown in the implant of prosthetic joints. The femoral component 24 has a pair of laterally spaced apart condylar elements 30 and a stem 32 unitary with and extending superiorly longitudinally upwardly for affixation in the natural femur (not shown) in a well-known manner. A tibial bearing member 40 selected from a plurality of tibial bearing members made available for use in connection with the system of the invention is interposed between the tibial component 22 and the femoral component 24 and is carried by the tray element 26 for supporting the condylar elements 30 of the femoral component 24, as will be described in greater detail below.

Bearing member 40 has a pair of articular surfaces 42 upon which the condylar elements 30 are disposed in the implanted knee prosthesis 20. Bearing member 40 is formed of a suitable biocompatible bearing material, such as high-density polyethylene, and preferably is constructed in one piece, including a base 44 and a tibial eminence in the form of a projection 46 extending generally longitudinally upwardly in a superior direction from the base 44 toward the femoral component 24. A recess in the form of a bore 48 passes through the projection 46 and has a diameter generally complementary to the outer diameter of a stabilizing post 50 for purposes which will be described below.

Figure 2:
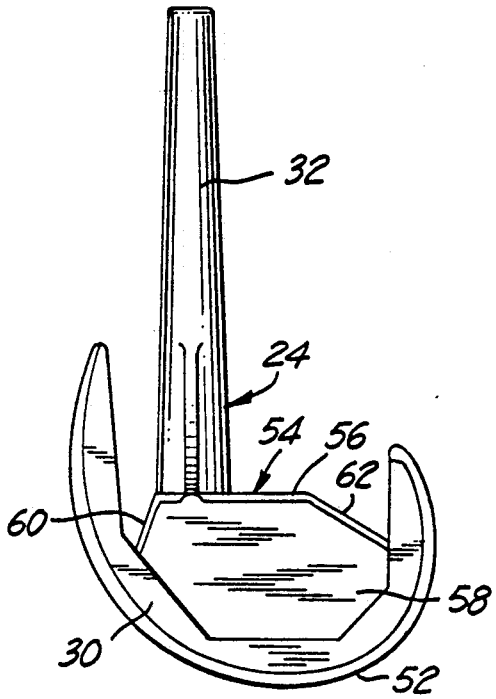
FIG. 2 is a side elevational view of the femoral component of the knee prosthesis.
Figure 3:
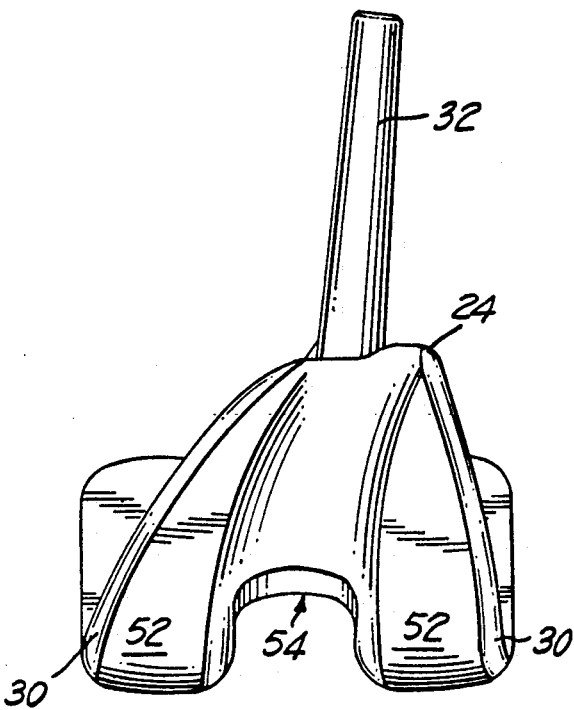
FIG. 3 is a front elevational view of the femoral component.
Figure 4:
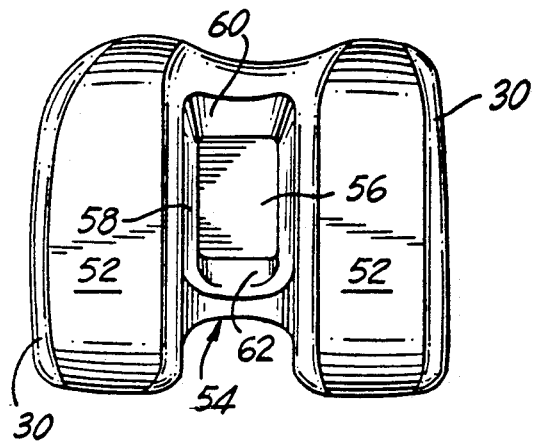
FIG. 4 is a bottom plan view of the femoral component.

As best seen in FIGS. 2 through 4, as well as in FIG. 1, femoral component 24 is constructed in one piece, preferably of a biocompatible high-strength alloy, such as a cobalt-chrome alloy, and includes articular surfaces 52 on the condylar elements 30 for engaging the articular surfaces 42 of the bearing member 40. A box-like bridging portion 54 lies between the condylar elements 30 and is open downwardly toward the tibial component 22. Boxlike bridging portion 54 includes an uppermost superior top wall 56, laterally spaced apart side walls 58, an anterior wall 60, and a posterior wall 62.

Figure 5:
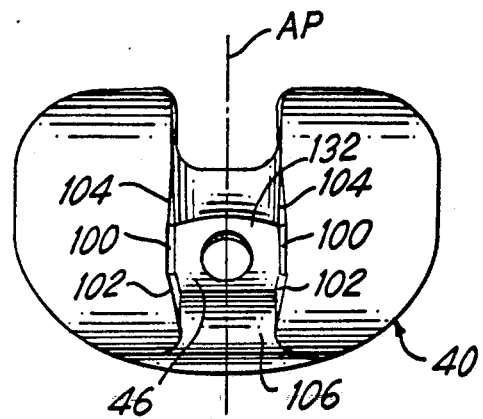
FIG. 5 is a top plan view of one tibial bearing member of the knee prosthesis system of the invention.

Turning now to FIGS. 5 through 7, as well as to FIG. 1, tibial component 22 also is constructed in one piece, preferably of the same biocompatible high-strength alloy as femoral component 24. Tray element 26 includes a platform 64 and a lip 66 extending around the perimeter of the platform 64. The base 44 of bearing member 40 has a peripheral groove 68 which establishes a basal pad 70 and a surrounding shoulder 72 so that upon seating of the base 44 upon the tray element 26, the basal pad 70 rests upon the platform 64 and the shoulder 72 overlies the lip 66. Lip 66 is undercut at 74, adjacent posterior portions 76 of the tray element 26, to establish grooves 78 beneath the lip 66 at those locations. Basal pad 70 also is undercut at 80, adjacent corresponding posterior portions 82 of the bearing member 40, to establish tongues 84 projecting in a posterior direction. A lock wire 86 is located at the anterior portion 88 of the basal pad 70 and straddles a plurality of anterior notches 90 in the basal pad 70. Tabs 92 on corresponding anterior portions of the lip 66 project in a posterior direction so that the bearing member 40 is selectively secured to the tray element 26 of the tibial component 22 by the securing means provided by the above-described structure, as follows. The tongues 84 at the posterior portions 82 of the bearing member 40 are inserted into the corresponding grooves 78 beneath the lip 66 at posterior portions 76 of the tray element 26, the anterior notches 90 are registered with the tabs 92, and the bearing member 40 is urged toward the tray element 26 until the lock wire 86 snaps over the tabs 92 and is captured beneath the tabs 92 to secure the bearing member 40 in place upon the tray element 26. Thus, the resilience of the lock wire 86, coupled with the arrangement of the notches 90 and the tabs 92, serves as a detent mechanism for the selective securement of the bearing member 40 to the tibial component 22. The ease with which the bearing member 40 is affixed to the tibial component 22 enables the surgeon to select a bearing member 40 of appropriate size and interoperatively fit the bearing member 40 to implanted tibial and femoral components 22 and 24 without disturbing the implanted components. The implant procedure is simplified and facilitated by the ability to implant tibial and femoral components of standard size and configuration and then to compensate for the dimensional needs of a particular patient by the interoperative utilization of provisional trials to arrive at a bearing member of appropriate joint space dimensions to achieve optimum fit and performance. In particular, the above arrangement enables a wider range of fit with a reduced number of sizes required in the femoral component 24.

Once the bearing member 40 is seated upon and affixed to the tray element 26 of the tibial component 22, the articular surfaces 52 of the condylar elements 30 of the femoral component 24 are engaged with the corresponding articular surfaces 42 of the bearing member 40, as illustrated in FIG. 7. The tibial eminence provided by projection 46 is received within the box-like bridging portion 54 to provide controlled restraint against excessive relative movement, including lateral and medial movements, varus and valgus movements, and anterior-posterior movements, between the femoral component 24 and the tibial component 22 so that the knee prosthesis 20 enables movements which emulate the natural knee and restore the natural knee function to a greater degree, while unwanted displacements and dislocation are resisted. With respect to relative lateral and medial movements, and varus and valgus movements, the lateral side walls 58 of the bridging portion 54 converge slightly in the superior, or longitudinal upward direction, as illustrated by angle S, and the corresponding side walls 100 of projection 46 are essentially parallel to the side walls 58 of the bridging portion 54. Some clearance is provided between the corresponding side walls 58 and 100 for enabling slight relative lateral and medial movements, and for permitting some varus and valgus movements, with controlled restraint. Angle S preferably is about 3°.

Returning briefly to FIG. 5, the side walls 100 of the projection 46 are provided with lateral surface portions 102 adjacent the anterior of the projection 46 and lateral surface portions 104 adjacent the posterior of the projection 46, all of the lateral surface portions 102 and 104 being angled with respect to anterior-posterior planes, such as plane AP, so as to enable limited relative rotation between the femoral component 24 and the tibial component 22 about the longitudinal direction. The amount of such permitted rotation varies with flexion of the knee prosthesis 20, which flexion will be described below. The permitted rotation is minimal at hyperextension and is limited to about 8° of rotation in either direction at a flexion of about 10°, to about 11° of rotation in either direction at about 90° of flexion. Such limited rotation renders the knee prosthesis 20 less sensitive to precise alignment of the tibial and femoral components 22 and 24 during implant and accommodates some misalignment, without adversely affecting performance, thereby facilitating the implant procedure. Dynamic performance of the implanted knee prosthesis 20 is enhanced by enabling some relative displacement of the components of the prosthesis, as described above, with controlled restraint against excessive relative movements.

Figure 8:
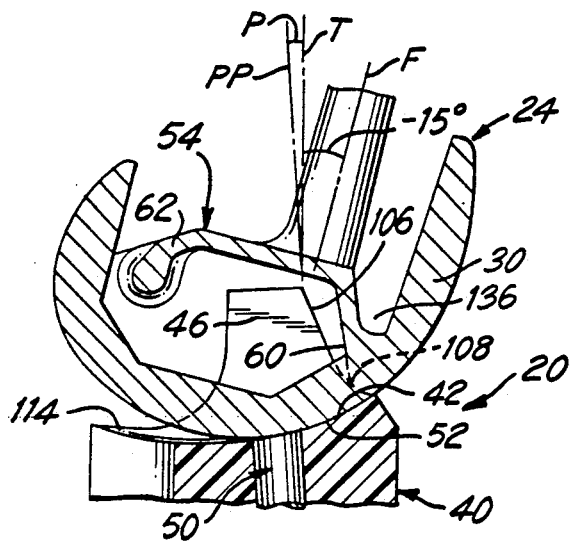
Figure 9:
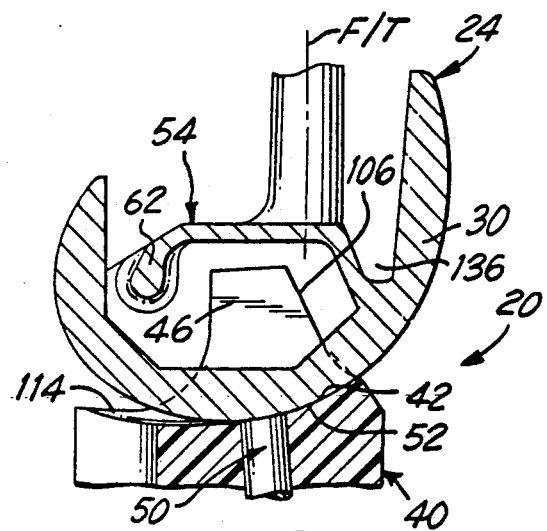
Figure 10:
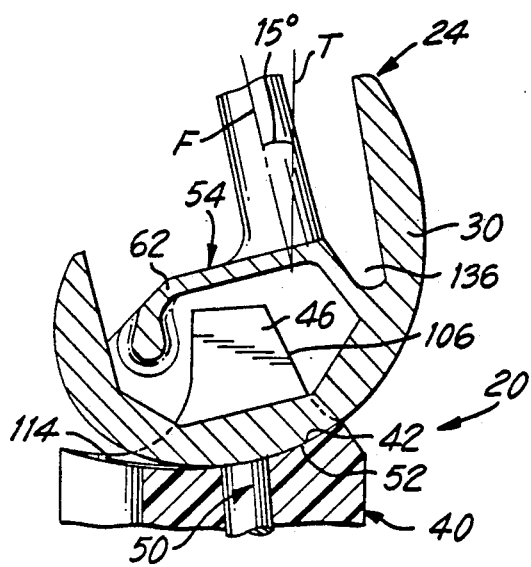
Figure 11:
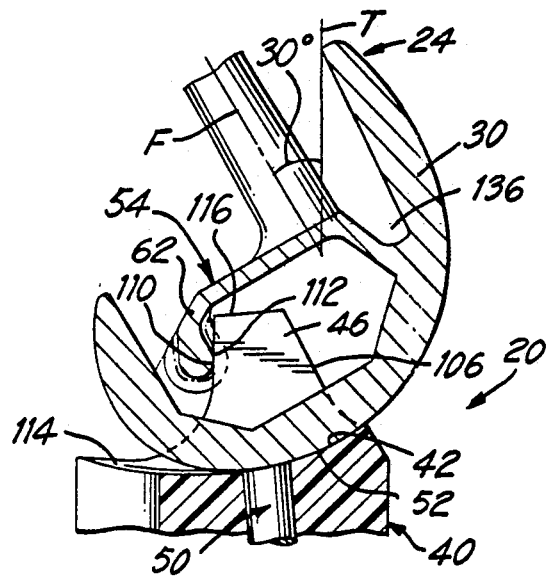
Figure 12:
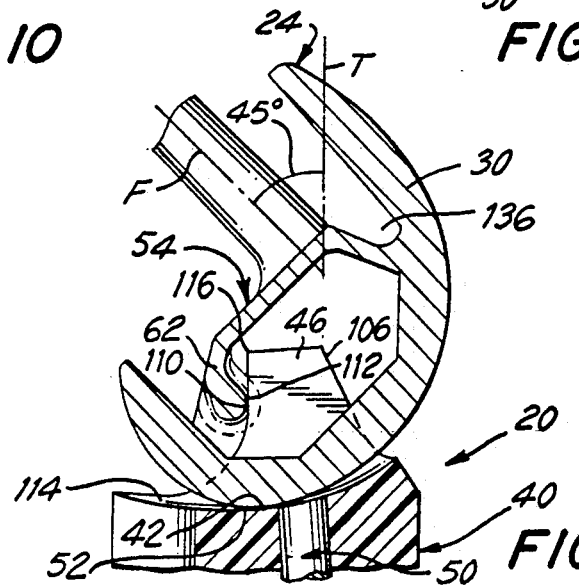
Figure 13:
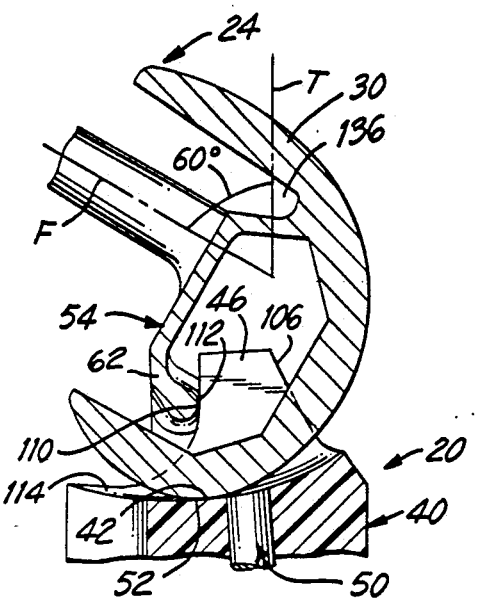
Figure 14:
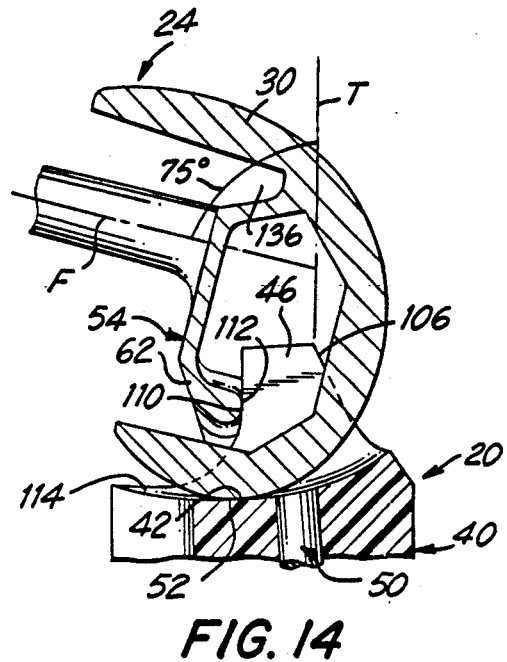
Figure 15:
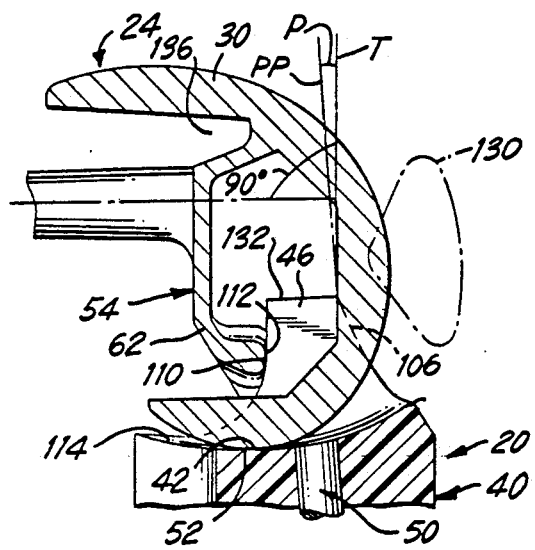
Figure 16:
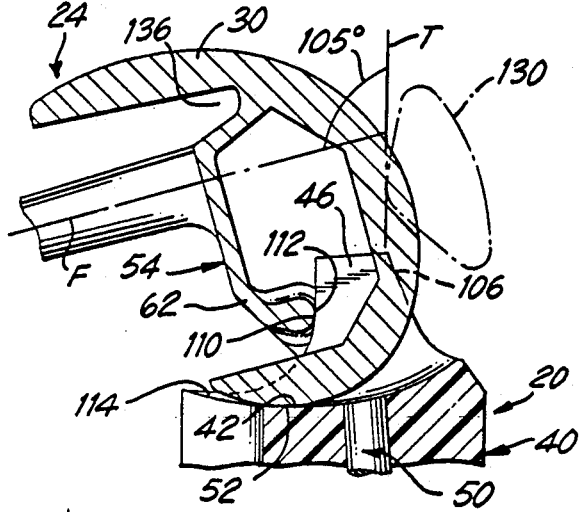
Figure 17:
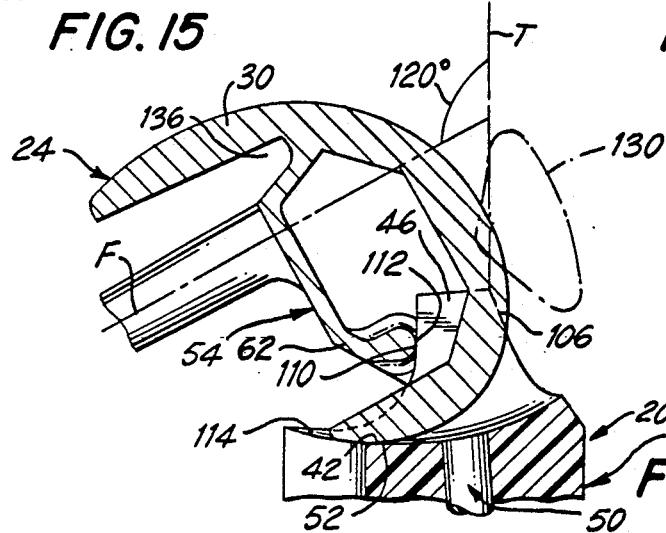

Referring now to FIGS. 8 through 17, the eminence provided by projection 46 controls relative movement between the tibial component 22 and the femoral component 24 in anterior-posterior directions in the following manner. FIG. 8 illustrates, diagrammatically, the knee prosthesis 20 at one limit of the range of flexion, namely, at 15° of hyperextension, as shown by the orientation of the axis F of the femoral component 24 at −15° relative to the axis T of the tibial component 22. At the illustrated hyperextended position, further hyperextension is precluded by the impingement of the anterior wall 60 of the bridging portion 54 on the corresponding anterior surface 106 of projection 46, as shown at 108. The articular surfaces 52 of the condylar elements 30 of the femoral component 24 are engaged with anterior portions of the articular surfaces 42 of bearing member 40. As knee prosthesis 20 experiences flexion away from the −15° hyperextension illustrated in FIG. 8, as shown in FIG. 9, which illustrates the component parts at 30° flexion, and in FIG. 10, which illustrates the component parts at 15° flexion, the projection 46 is not engaged with the bridging portion 54 and some freedom for relative anterior-posterior movement is permitted. However, upon reaching 30° of flexion, as shown in FIG. 11, a cam surface 110 along the posterior of the projection 46 is engaged by a follower 112 on the posterior wall 62 of the bridging member 54 so that relative anterior-posterior movement is controlled by the contour of the cam surface 110. As flexion is continued, the follower 112 follows cam surface 110 to provide controlled relative anterior-posterior movement. Thus, as illustrated in FIGS. 12 through 17, the follower 112 remains engaged with the cam surface 110 through 45° of flexion, as depicted in FIG. 12, through 60° of flexion, as depicted in FIG. 13, through 75° of flexion, as depicted in FIG. 14, through 90° of flexion, as depicted in FIG. 15, through 105° of flexion, as depicted in FIG. 16, to 120° of flexion, as shown in FIG. 17, to complete the full range of flexion between about −15° and about 120° of flexion. Throughout the portion of the range of flexion, between 30° and 120°, in which portion the follower 112 is engaged with the cam surface 110, the follower 112 remains engaged with the projection 46 more closely adjacent the inferior or lower end 114 of the projection 46 than the superior or upper end 116 of the projection 46 so as to maintain at a minimum the load placed on the projection 46 at the lower end 114 by the moment acting upon the projection 46.

It is noted that the commencement of the controlled movement and concomitant restraint accomplished by engagement of the follower 112 with the cam surface 110 at about 30° of flexion is advantageous in that stability in the knee prosthesis 20 is accomplished at such critical occasions as walking up stairs, rising from a seated position or walking up or down a low grade, thus reducing unwanted displacements and the possibility of dislocation at these critical movements. The desired controlled movement and concomitant restraint comes into play at almost any deviation from a level gate and assists in maintaining an appropriate gate cycle when deviating from a level gate, such as in negotiating an incline.

The material of bearing member 40 is selected for lubricity characteristics and does not possess the high strength exhibited in the materials selected for the tibial component 22 and the femoral component 24. Accordingly, the stresses experienced by the projection 46 tend to bend the projection 46, resulting in interruption of the proper function of the projection 46 and a consequent instability in the operation of the knee prosthesis 20. In addition, deformation of the material of the projection 46 eventually can lead to complete and catastrophic failure of the projection 46. In order to stabilize the projection 46, and at the same time reinforce the material of the projection 46 against failure due to the loads imposed on the projection during service, the stabilizing post 50 is placed within the bore 48 in the projection 46. Stabilizing post 50 preferably is constructed of the same high-strength alloy as the material of the tibial and femoral components 22 and 24, and includes a stabilizing portion 120 adjacent the superior or upper end 121 of the stabilizing post 50, which stabilizing portion 120 projects superiorly or upwardly from the tray element 26 of the tibial component 22 and is complementary with the bore 48 in the projection 46 so as to extend into the projection 46 and stabilize the projection 46 against the forces applied to the projection 46 as a result of the above-described function of the projection 46. The stabilizing post 50 is secured to the tibial component 22 by securing means in the form of a pin portion 122, located at the lower end of the stabilizing post 50, and a complementary socket 124 in the tibial component 22. The relative dimensions of the pin portion 122 and the socket 124 are such that the pin portion 122 may be inserted into the socket 1224 with a fit which will retain the stabilizing post 50 secured to the tibial component 22. A chamfer 126 at the inferior or lower end of the stabilizing post 50 facilitates the insertion of the stabilizing post 50 into the bore 48 and into the socket 124. At the same time, a plurality of ribs 128 located at spaced intervals along the stabilizing portion 120 of stabilizing post 50, adjacent the superior or upper end 121 of the stabilizing post 50, will be engaged positively with the material of the bearing member 40 to assist in securing the bearing member 40 seated upon tray element 26. The modular feature provided by the separate bearing member 40 and the stabilizing post 50 enables the surgeon to choose the appropriate bearing member 40, along with the corresponding stabilizing post 50, for assembly interoperatively during the implant procedure.

The incorporation of stabilizing post 50 enables better management of the material of bearing member 40, and in particular, the material of the eminence provided by projection 46. Thus, as seen in FIG. 17, the projection 46 is canted posteriorly, as illustrated by the small angle P between the axis PP of the projection 46 and the vertical, or superior-inferior direction, as represented by axis T, so that as the knee prosthesis 20 experiences flexion from about 90° to about 120°, as illustrated in FIGS. 15 through 17, exposure of the projection 46 to the patella, shown in phantom at 130, is minimized and impingement of the patella against the projection 46 is precluded. In this manner, the patella is allowed to ride freely on the condylar elements 30 of the femoral component 24, without being intercepted by the eminence provided by projection 46, for more closely emulating the natural knee. An angle P of about 3° is adequate to attain the desired result. The reinforcement provided by stabilizing post 50 is enhanced, while the material of the projection 46 is carefully managed, by canting the stabilizing post 50 at the same angle P relative to the vertical direction to assure that the stabilizing post 50 extends downwardly into the stem 28 of the tibial component. Superior surface 132 of the projection 46 is essentially normal to the axis PP and the corresponding superior end 121 of the stabilizing post 50 is maintained flush with the superior surface 132 of the projection 46. The employment of angle P and the consequent elimination of the impingement of the patella on the projection 46 provides appropriate patella tracking throughout a range of locations of the joint line, thus rendering the knee prosthesis 20 less sensitive to precise placement of the tibial component 22 and the femoral component 24 relative to one another in the vertical, or superior-inferior direction. Some variation in the placement with respect to the natural joint line is therefore accommodated and the surgeon is provided with greater latitude during the implant procedure. In addition, the presence of angle P enables the superior portions of anterior wall 62 of bridging portion 54 likewise to be canted posteriorly without impinging against the projection 46 at hyperextension and at lower angles of flexion, as seen in FIGS. 8 and 9, minimizing resection of the bone of the femur which will be located in vicinity 136, with concomitant conservation of femoral bone tissue, for implant of the femoral component 24.

Bearing member 40 is supplied not only in various sizes and dimensions for meeting the requirements of fit and articulation in a particular patient, but also is provided with variations in the extent of control of relative movements enabled by differences in the dimensions, and especially in the height, of the eminence provided by projection 46. Thus, the surgeon may select the degree of control desired by selecting the appropriate bearing member 40. In addition, should it become necessary to revise the knee prosthesis after extended service, as a result of further deterioration of the natural soft tissue balances available at the knee over time, the surgeon is able to replace the bearing ring member 40 without disturbing the implanted tibial component 22 or femoral component 24, so that the system of the present invention facilitates selection of the extent of control not only upon initial implant, but upon revision to correct for subsequent changes in conditions at the implant site.

It will be seen that the present invention attains freedom of motion to simulate movements available in the natural knee joint so as to restore more fully the natural function of the knee, while providing the stability necessary to resist unwanted movements and dislocation; provides the requisite strength to withstand the stresses encountered during service, without excessive wear or catastrophic failure; facilitates the implant procedure, as well as any subsequent revision of the knee prosthesis which may become necessary, by providing a modular system which enables the selection and interoperative insertion of an appropriate tibial bearing member, independent of the implant of the femoral component and the tibial component of the prosthetic implant; requires minimal bone resection and attains a concomitant reduction in the invasion of the natural bone; is less sensitive to precise placement, thereby simplifying the implant procedure; accommodates some misalignment of the components of the prosthesis, without compromising performance; and provides exceptional performance over an extended service life.

It is to be understood that the above detailed description of a preferred embodiment of the invention is provided by way of example only. Various details of design and construction may be modified without departing from the true spirit and scope of the invention, as set forth in the appended claims.

The embodiments of the invention in which an exclusive property of privilege is claimed are defined as follows:

1. In a knee prosthesis system for a prosthetic knee, the knee prosthesis system including a tibial component having a tray element, a femoral component having laterally spaced apart condylar elements, and a selectable bearing member to be carried by the tray element of the tibial component for supporting the condylar elements of the femoral component of operation of the knee prosthesis, including flexion of the prosthetic knee, the bearing member being constructed of a bearing material and having an integral eminence of bearing material projecting superiorly longitudinally upwardly from an inferior end adjacent the tibial component toward a superior end adjacent the tibial component for reception between the condylar elements of the femoral component to provide controlled restraint against excessive relative movement between the femoral component and the tibial component, control of the anterior-posterior portions of the relative movement being provided by a cam surface on the eminence and a follower on the femoral component for following the cam surface, the improvement comprising:

a stabilizing post including a stabilizing portion for projecting superiorly from the tibial component toward the femoral component; and a recess in the eminence, the recess including a recess portion so complementary to the stabilizing portion of the stabilizing post such that when the bearing member is seated on the tray element of the tibial component, the stabilizing portion of the stabilizing post comprises means on the stabilizing post located within the recess portion of the recess in such complementary relationship with the recess portion as to be engaged positively with the material of the eminence along the recess portion so as to reinforce and stabilize the material of the eminence against forces exerted upon the eminence during operation of the knee prosthesis.

2. The improvement of claim 1 wherein the eminence is canted posteriorly at a relatively small angle to the longitudinal direction so as to reduce exposure of the eminence to the patella during flexion of the prosthetic knee.

3. The improvement of claim 2 wherein the relatively small angle is approximately 3°.

4. The improvement of claim 2 wherein at least the stabilizing portion of the stabilizing post is canted posteriorly at a relatively small angle to the longitudinal direction.

5. The improvement of claim 4 wherein the relatively small angle of the stabilizing portion is essentially the same as the relatively small angle of the eminence.

6. The improvement of claim 5 wherein each relatively small angle is approximately 3°.

7. The improvement of claim 1 wherein the range of flexion extends from a hyperextended position to a fully flexed position, and the cam surface and follower are arranged such that the follower is disengaged from the cam surface in the portion of the range from the hyperextended position through about 30° of flexion and then is engaged with the cam surface from about 30° of flexion to the fully flexed position.

8. The improvement of claim 7 wherein the range of flexion extends from about 15° of hyperextension to about 120° of full flexion.

9. The improvement of claim 7 wherein the follower engages the cam surface more closely adjacent the inferior end of the eminence than the superior end.

10. The improvement of claim 1 wherein the femoral component includes lateral side walls between which the eminence will extend and the eminence includes lateral surfaces having portions essentially parallel to the lateral side walls of the femoral component, and further portions angled slightly with respect to anterior-posterior planes for enabling limited relative rotation between the tibial component and the femoral component about the longitudinal direction in which the eminence projects, within a limited portion of the range of flexion.

11. The improvement of claim 10 wherein the limited rotation is minimal at the hyperextended position and is in the range of about 8° of rotation in directions away from the anterior-posterior planes at about 10° of flexion, to about 11° of rotation in directions away from the anterior--posterior planes at about 90° of flexion.

12. The improvement of claim 1 including selective securing means having complementary securing elements on the tibial component and on the bearing member for enabling the selective interoperative securement of the bearing member on the tibial component.

13. The improvement of claim 12 wherein the selective securing means includes a detent lock wire on the bearing member and a corresponding detent tab on the tray of the tibial component, the detent lock wire being located so as to catch beneath the detent tab upon seating of the bearing member on the tray.

14. The improvement of claim 1 wherein the means on the stabilizing post includes a plurality of ribs located at spaced intervals along the stabilized portion of the stabilizing post such that upon seating of the bearing member on the tray element of the tibial component, the stabilizing portion of the stabilizing post will enter the recess portion of the recess and the ribs will engage the material of the bearing member to reinforce and stabilize the eminence against forces exerted upon the eminence during operation of the knee prosthesis.

15. The improvement of claim 14 wherein the tibial component has an inferiorly depending stem, and the stabilizing post extends inferiorly into the stem of the tibial component.

16. The improvement of claim 14 wherein the stabilizing post includes a pin portion adjacent the inferior end of the stabilizing post, and the tibial component includes a socket in the tibial component, the relative dimensions of the socket and the pin portion being such that the pin portion may be inserted interoperatively into the socket.

17. The improvement of claim 16 wherein the tibial component has an inferiorly depending stem, and the pin portion of the stabilizing post and the socket in the tibial component each extend inferiorly into the stem.

18. In a knee prosthesis system for a prosthetic knee, the knee prosthesis system including a tibial component having a tray element, a femoral component having laterally spaced apart condylar elements, and a selectable bearing member to be carried by the tray element of the tibial component for supporting the condylar elements of the femoral component for operation of the knee prosthesis, including flexion of the prosthetic knee, the bearing member having an integral eminence projecting superiorly longitudinally upward from an inferior end adjacent the tibial component toward a superior end adjacent the femoral component for reception between the condylar elements of the femoral component to provide controlled restraint against excessive relative movement between the femoral component and the tibial component, control of the anterior-posterior portions of the relative movement being provided by a cam surface on the eminence and a follower on the femoral component for following the cam surface, the improvement wherein the range of flexion extends from a hyperextended position to a fully flexed position, and the cam surface and follower are arranged such that the follower is disengaged from the cam surface in the portion of the range from the hyperextended position through about 30° of flexion and then is engaged with the cam surface from about 30° of flexion to the fully flexed position.

19. The improvement of claim 18 wherein the range of flexion extends from about 15° of hyperextension to about 120° of full flexion.

20. The improvement of claim 19 wherein the follower engages the cam surface more closely adjacent the inferior end of the eminence than the superior end.

21. In a knee prosthesis system for a prosthetic knee, the knee prosthesis system including a tibial component having a tray element, a femoral component having laterally spaced apart condylar elements, and a selectable bearing member to be carried by the tray element of the tibial component for supporting the condylar elements of the femoral component for operation of the knee prosthesis, including flexion of the prosthetic knee, the bearing member having an integral eminence projecting superiorly longitudinally upwardly from an inferior end adjacent the tibial component toward a superior end adjacent the femoral component for reception between the condylar elements of the femoral component, the femoral component including lateral side walls between which the eminence will extend, to provide controlled restraint against excessive relative movement between the femoral component and the tibial component, control of the anterior-posterior portions of the relative movement being provided by a cam surface on the eminence and a follower on the femoral component for following the cam surface, the improvement wherein the eminence includes lateral surfaces having portions essentially parallel to the lateral side walls of the femoral component, and further portions angled slightly with respect to anterior-posterior planes for enabling limited relative rotation between the tibial component and the femoral component about the longitudinal direction in which the eminence projects, within a limited portion of the range of flexion.

22. The improvement of claim 21 wherein the limited rotation is minimal at the hyperextended position and is in the range of about 8° of rotation inn directions away from the anterior-posterior planes at about 10° of flexion, to about 11° of rotation in directions away from the anterior-posterior planes at about 90° of flexion.

* * * * *